(12) United States Patent
Cavalieri et al.

(10) Patent No.: US 8,235,925 B2
(45) Date of Patent: Aug. 7, 2012

(54) BACK BRACE

(75) Inventors: William Cavalieri, Tarpon Springs, FL (US); William Cavalieri, Jr., Holiday, FL (US)

(73) Assignee: William Cavalieri, Sr., New Port Richey, FL (US)

( * ) Notice: Subject to any disclaimer, the term of this patent is extended or adjusted under 35 U.S.C. 154(b) by 272 days.

(21) Appl. No.: 12/333,730

(22) Filed: Dec. 12, 2008

(65) Prior Publication Data

US 2009/0156972 A1    Jun. 18, 2009

Related U.S. Application Data

(60) Provisional application No. 61/014,032, filed on Dec. 15, 2007.

(51) Int. Cl.
*A61F 5/00*    (2006.01)
*A61F 5/24*    (2006.01)
*A61G 15/00*    (2006.01)

(52) U.S. Cl. ....... 602/19; 128/96.1; 128/845; 128/115.1

(58) Field of Classification Search .................... 602/19; 128/96.1, 845, 115.1

See application file for complete search history.

(56) References Cited

U.S. PATENT DOCUMENTS

| | | |
|---|---|---|
| 3,871,367 A | 3/1975 | Miller |
| 4,173,973 A | 11/1979 | Hendricks |
| RE31,564 E | 4/1984 | Hendricks |
| 4,459,979 A | 7/1984 | Lewis, Jr. |
| 4,508,110 A | 4/1985 | Modglin |
| 4,541,419 A | 9/1985 | Osawa |
| 4,572,167 A | 2/1986 | Brunswick |
| 5,074,292 A | 12/1991 | Cox |
| 5,433,697 A | 7/1995 | Cox |
| 5,690,609 A | 11/1997 | Heinze, III |
| 6,099,490 A | 8/2000 | Turtzo |
| 6,152,893 A | 11/2000 | Pigg et al. |
| 6,524,264 B1 * | 2/2003 | Hutchinson ..................... 602/19 |
| 7,329,231 B2 * | 2/2008 | Frank ............................. 602/19 |

* cited by examiner

*Primary Examiner* — Patricia Bianco
*Assistant Examiner* — Victoria J Hicks

(57) ABSTRACT

An application for a back brace for supporting both the abdomen and lower back of the user includes an abdominal support member and a lumbar support member having a convex dome facing inwardly towards the lumbar region of a wearer; the support members joined by two belts. The belts are positioned though a slot on each side of a member and are used to adjust the biasing force between the members. The device further includes sleeves over a central region of the members providing additional comfort.

13 Claims, 6 Drawing Sheets

BACK BRACE

CROSS-REFERENCE TO RELATED APPLICATION

This nonprovisional patent application claims priority to provisional application Ser. No. 61/014,032, titled "Back Belt," filed Dec. 15, 2007. The entire contents of all the above applications are hereby incorporated by reference.

FIELD OF THE INVENTION

The present invention relates to a brace for providing immobilization of the human back and more particularly to a brace for providing a back profile and simultaneous abdominal and lumbar support.

BACKGROUND

Spinal and lower back muscular pain is a common problem in many individuals. This type of pain, particularly among older or overweight individuals, can easily be aggravated during any type of body trauma such as heavy lifting or strenuous physical activity.

Prescription drugs must often be used to alleviate lower back pain which may not always be effective. Day to day activity requires movement of the back which can lead to further muscular aggravation, only to reach the point where all but the most potent pain relief medication is needed to have any effect.

In order to help alleviate lower back pain, prevent injury or aid in recovery, it is necessary to utilize a device which can provide support to the lower back to prevent muscular strain. In the past, many types of apparatus have been provided which help with this problem. These devices range from wrap-type supports to individual solid support fixtures placed longitudinally along the back to restrain movement. Many of these devices are either very heavy, too hot to wear, burdensome by unduly restricting movement or do not provide the proper support and alignment to be useful.

Recent research has determined that the most effective lumbar support occurs when the abdominal area of the user is supported as well. U.S. Pat. Nos. 4,572,167 and 4,508,110 show support devices which wrap around the user's body but do not provide adequate abdominal and lumbar support due to the flexibility of the material used in construction and the methods of attachment. U.S. Pat. Nos. 4,173,973, 4,541,419 and 3,871,367 teach devices which are awkward to wear and are incapable of simultaneous abdominal and lumbar support. Applicant's prior U.S. Pat. No. 5,074,292 issued December, 1991 shows a back brace that can be form fitted to the individual. Although the device performs its intended function, the present invention is an improvement that substantially uses an ideal lumbar configuration for improved muscle support. U.S. Pat. No. 5,433,697 teaches a conformable back belt with a lumbar support, but it has performance issues.

Thus, it is apparent from these types of prior art devices that it was necessary to provide a device which would provide simultaneous lumbar and abdominal support and alignment which is light, comfortable, and easily adjustable. The device should also lend itself to be worn not only while sedentary but during strenuous physical activity such as golf, tennis or other sports, or in the work place while one sits for long periods or any physical work is required.

SUMMARY OF THE INVENTION

The present invention is a back brace for supporting both the abdomen and lower back of the user including an abdominal support member and a lumbar support member. The lumbar support member has a convex dome facing inwardly towards the lumbar region of a wearer and the support members are joined by two belts. The belts are positioned though a side slot on each or each member. The side slots are used to adjust the biasing force between the members. The device further includes sleeves over a central region of the members providing additional comfort.

The lumbar support member includes a dome located on the back support member interfacing in the lower lumbar region of a wearer. The brace can easily be worn beneath or outside a wearer's clothing.

The support members preferably include rounded edges which are tapered for a comfortable fit along with a belt slots positioned one at each end of each support member. These slots are used to engage left and right fastening belts. Each belt includes hook and loop adjustable fasteners. Each belt is then positioned through a slot on each member. This enables both the abdominal and lumbar support members to be engaged separately to hold and shape both of the members firmly against the wearer by pulling on the belt ends and fastening them with the hook and loop material. Additionally, in some embodiments, a plurality of holes is placed about each support surface to allow body heat to escape.

In accordance with these and other objects which will become apparent hereinafter, the instant invention will now be described with particular reference to the accompanying drawings.

DETAILED DESCRIPTION OF THE FIGURES

The invention can be best understood by those having ordinary skill in the art by reference to the following detailed description when considered in conjunction with the accompanying drawings in which.

DETAILED DESCRIPTION OF THE INVENTION

Figure 1:
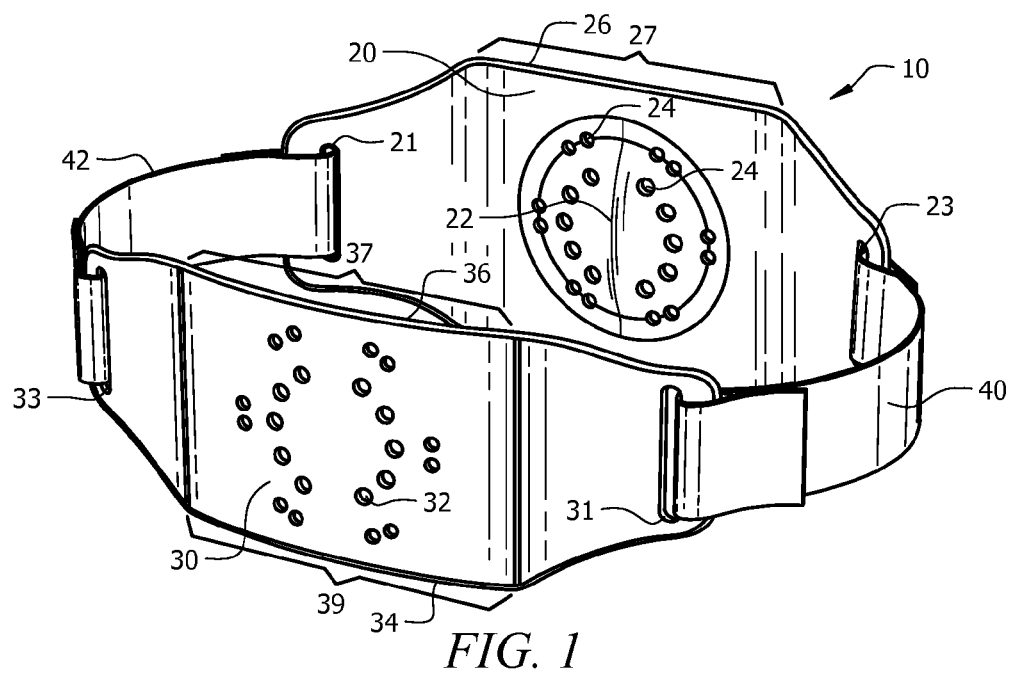
FIG. 1 illustrates a front perspective view of the invention.
Figure 2:
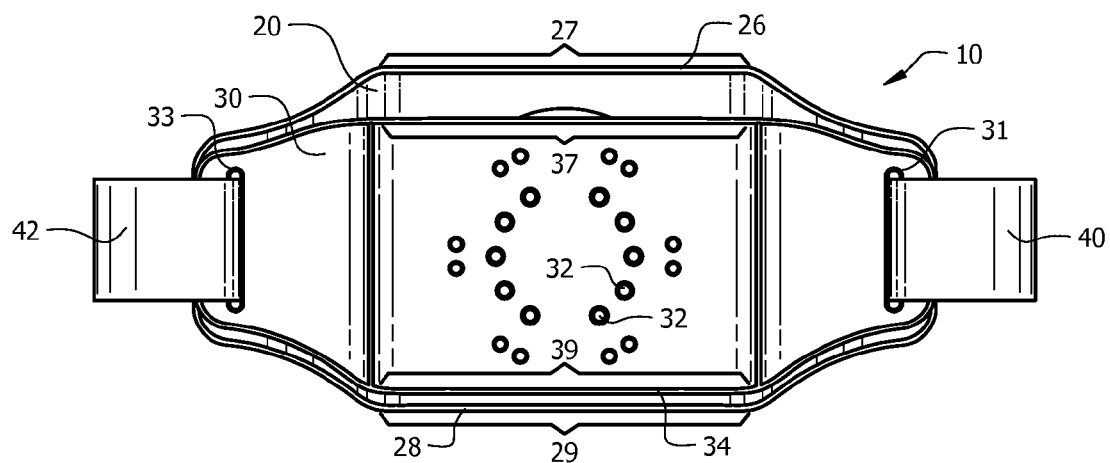
FIG. 2 illustrates a back perspective view of the present invention.
Figure 3:
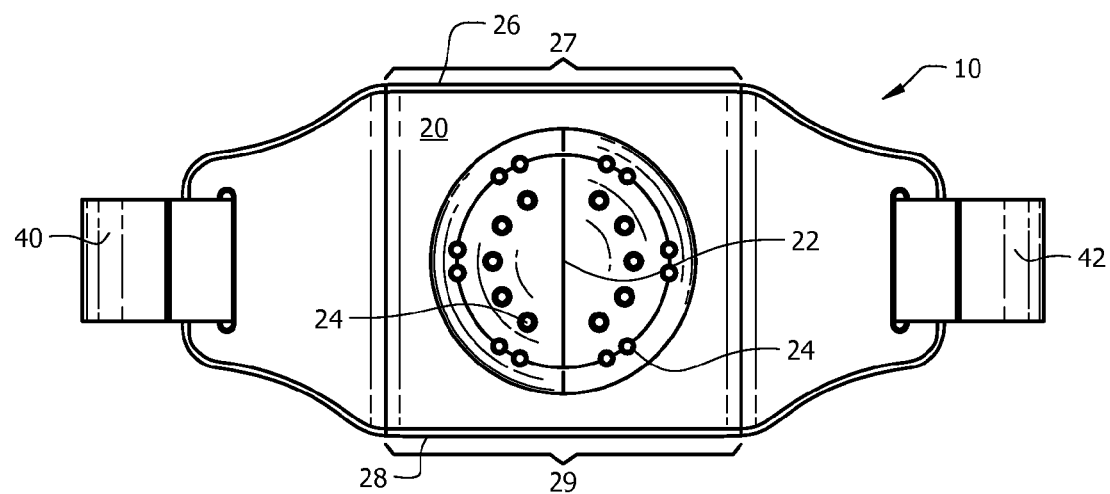
FIG. 3 illustrates a front elevational view of the present invention.
Figure 4:
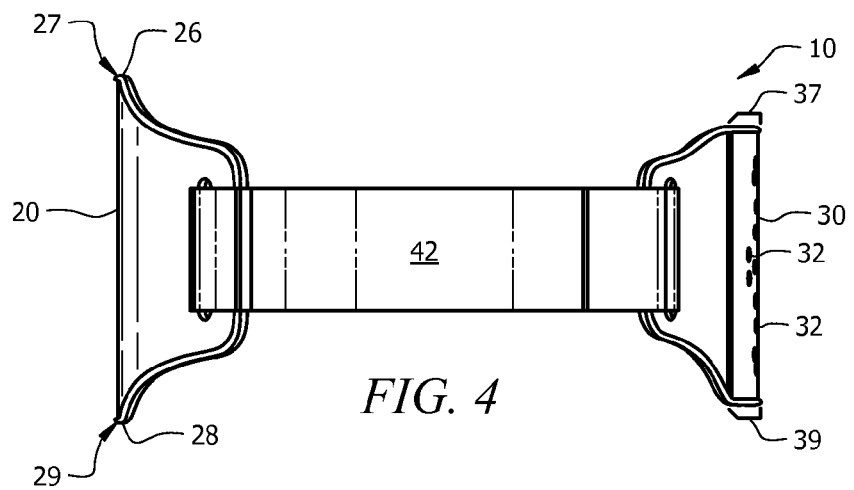
FIG. 4 illustrates a right-side elevational view of the lumbar member of the present invention.

Reference will now be made in detail to the presently preferred embodiments of the invention, examples of which are illustrated in the accompanying drawings. Throughout the following detailed description, the same reference numerals refer to the same elements in all figures.

As used throughout, the singular forms "a," "an" and "the" include plural referents unless the context clearly dictates otherwise. Thus, for example, reference to "a belt" can include two or more such belts unless the context indicates otherwise.

With reference to FIGS. 1-4, the back brace 10 includes an abdominal support member 30 and a lumbar support member 20. The abdominal support member 30 and lumbar support member 20 are generally outwardly convex in shape to conform to the peripheral torso shape of a human being in front and back body areas. The lumbar support member 20 includes a convex dome area 22 which is substantially at the center of the lumbar support member 20 and protrudes into the lower central lumbar back of the wearer to provide pressure to the human back contour. The lumbar support member 20 extends longitudinally across the surface of the lower back. The dome 22 protrudes convexly in the direction of the wearer, towards the lumbar region of the wearer's back.

This lumbar region of the lower back is often the most troublesome since it is difficult to support this area because of its shape. An advantage to the instant invention is the type of material and the specific dome shape used to adapt both the abdominal support member 30 and the lumbar support member 20 to a variety of users. In the preferred embodiment, the abdominal support member 30 and lumbar support member 20 are manufactured of a thermoplastic. However, as one skilled in the art can appreciate, the abdominal support member 30 and the lumbar support member 20 may be manufactured from any substantially rigid material.

The abdominal support member 30 includes a left vertical slot 31 at one end and a right vertical slot 33 at a second end. Likewise, the lumbar support member 20 includes a left vertical slot 23 at one end and a right vertical slot 21 at a second end. Each slot is wide and high enough to accommodate the left fastening belt 40 and right fastening belt 42. The fastening belts 40/42 bias the support members snugly against the user.

Figure 8:
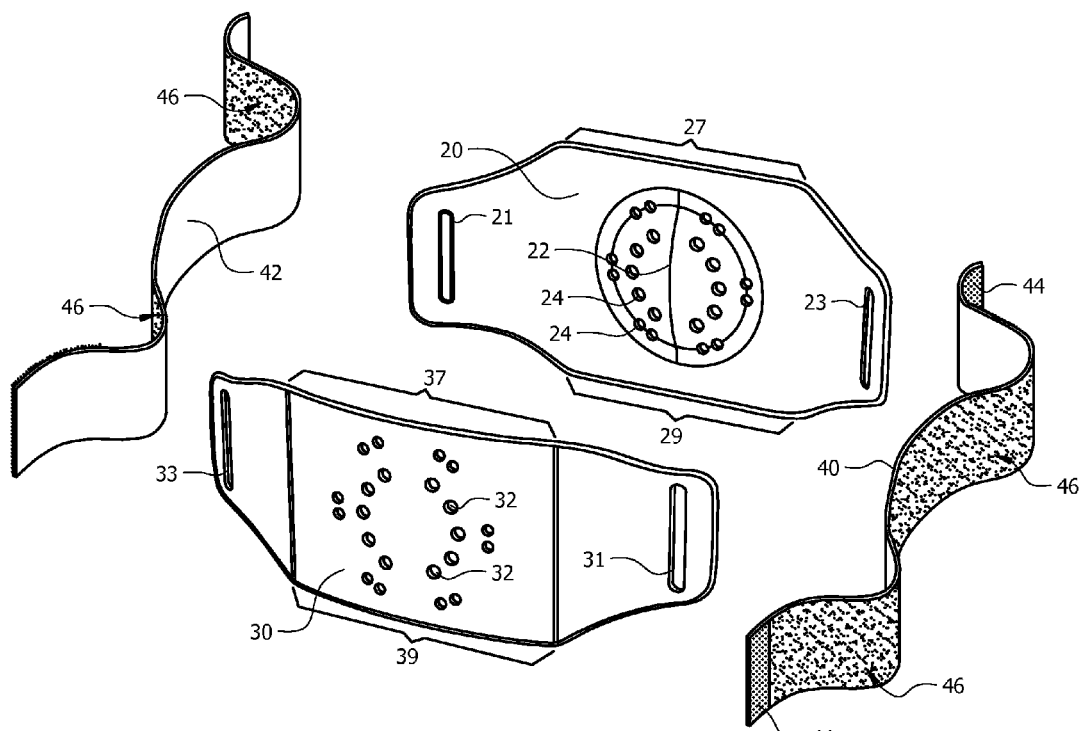
FIG. 8 illustrates an exploded view of the present invention.

In the preferred embodiment, the fastening belts 40/42 have hook material 44 (see FIG. 8) and loop material 46 (see FIG. 8). The left fastening belt 40 passes through the left vertical slot 31 of the abdominal support member 30 then passes through the left vertical slot 23 of the lumbar support member 20. The ends of the left fastening belt 40 have hook material 44 on an inside surface and the left fastening belt 40 has loop material 46 on the remainder of the inside surface. The hook material 44 removably fastens to the loop material 46, allowing a wide range of adjustments. Likewise, the right fastening belt 42 passes through the right vertical slot 33 of the abdominal support member 30 then passes through the right vertical slot 21 of the lumbar support member 20. The ends of the right fastening belt 42 have hook material 44 on an inside surface and the right fastening belt 42 has loop material 46 on the remainder of the inside surface. The hook material 44 removably fastens to the loop material 46, allowing a wide range of adjustments on this side. It is anticipated that the hook and loop material 44/46 is reversed in some embodiments.

The left fastening belt 40 and right fastening belt 42 are preferably made of a light weight, heavy duty nylon which aids in making the device lightweight and comfortable to wear. Any material with sufficient tensile strength is anticipated.

Figure 5:
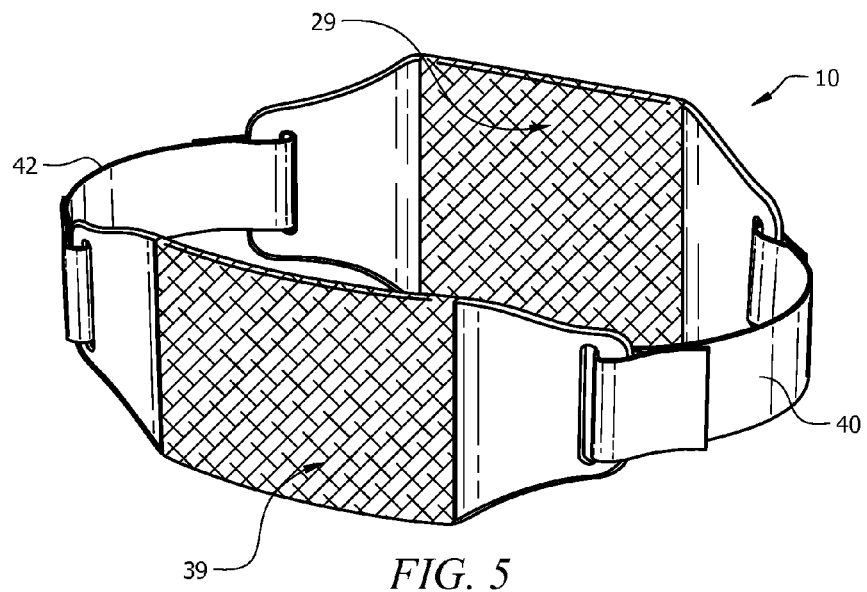
FIG. 5 illustrates a perspective view of the present invention with sleeves.
Figure 6:
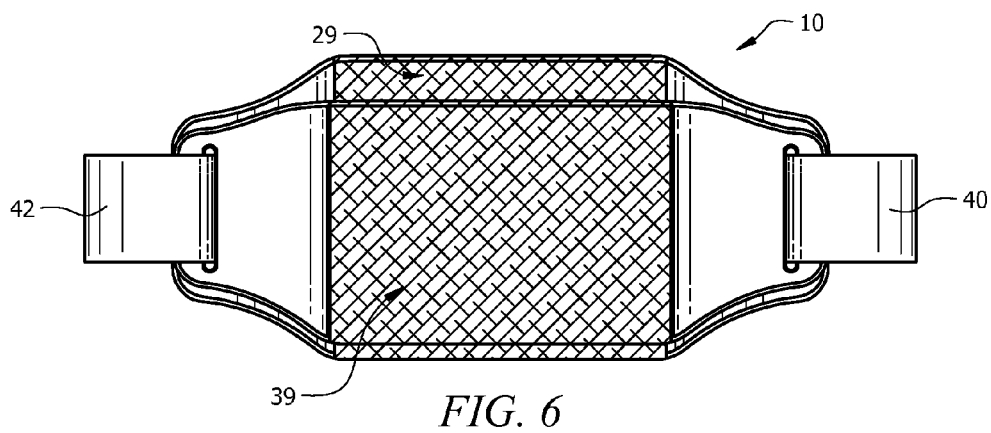
FIG. 6 illustrates a front elevational view of the present invention with sleeves.

The central area of the abdominal support member 30 and lumbar support member 20 are substantially rectangular in shape and include rounded corners which are tapered. This provides greater comfort to the user when the back belt 10 is securely fastened around the torso, applying as much biasing force as needed using the left and/or right fastening belts 40/42. Without these tapered end corners, the brace would quickly become uncomfortable due to excessive force applied at these pressure points. Being square, the top edge 36 and the bottom edge 34 of the center section of the abdominal support member 30 are substantially straight. Likewise, the top edge 26 and the bottom edge 28 of the center section of the lumbar support member 20 are also substantially straight. This provides for a proper surface for attaching the removable lumbar sleeve 39 and the removable abdominal sleeve 29 as shown in FIGS. 5 and 6.

The abdominal support member top central edge 37 is the portion of the top edge 36 of the abdominal support member 30 that is substantially straight. The abdominal support member bottom central edge 39 is the portion of the bottom edge 34 of the abdominal support member 30 that is substantially straight. The lumbar support member top central edge 27 is the portion of the top edge 26 of the lumbar support member 20 that is substantially straight. The lumbar support member bottom central edge 29 is the portion of the bottom edge 28 of the lumbar support member 20 that is substantially straight.

For ease of description, the following abdominal support member 30 distances are defined:
   a first vertical distance between the top of the left slot 31 of the abdominal support member 30 and the top central edge 37 of the abdominal support member 30,
   a second vertical distance between the top central edge 37 of the abdominal support member 30 and the top of the right slot 33 of the abdominal support member 30,
   a third vertical distance between the bottom of the left slot 31 of the abdominal support member 30 and the bottom central edge 39 of the abdominal support member 30, and
   a fourth vertical distance between the bottom of the right slot 33 of the abdominal support member 30 and the bottom central edge 39 of the abdominal support member 30.

For ease of description, the following distances along the lumbar support member 30 are defined:
   a fifth vertical distance between the top of the left slot 23 of the lumbar support member 20 and the top central edge 27 of the lumbar support member 20.
   a sixth vertical distance between the top central edge 27 of the lumbar support member 20 and the top of the right slot 21 of the lumbar support member 20,
   a seventh vertical distance between the bottom of the left slot 23 of the lumbar support member 20 and the bottom central edge 29 of the lumbar support member 20, and
   an eighth vertical distance between the bottom of the right slot 21 of the lumbar support member 20 and the bottom central edge 29 of the lumbar support member 20.

The abdominal support member 30 includes a plurality of vents 32 and the lumbar support member 20 includes a plurality of vents 24. Both abdominal support vents 32 and lumbar support vents 24 prevent an excess buildup of body heat under each member 20/30 and allow air to circulate under each respective member 20/30, especially during exercise or strenuous activity.

Additionally, in one embodiment as shown in FIGS. 5 and 6, the support members 20/30 include covering sleeves 29/39 with a breathable substance, such as GORTEX®, or the like. In some embodiments, the support members 20/30 include covering sleeves 29/39 made of a material such as NEOPRENE®. In some embodiments, the covering sleeves 29/39 are thick enough as to provide padding. The first sleeve 39 covers the abdominal support member 30 (front and back surfaces) between the top edge 36 and the bottom edge 34 of the center section. Likewise, a second sleeve 29 covers the lumbar support member 20 between the top edge 26 and the bottom edge 28 of the center section.

Figure 7:
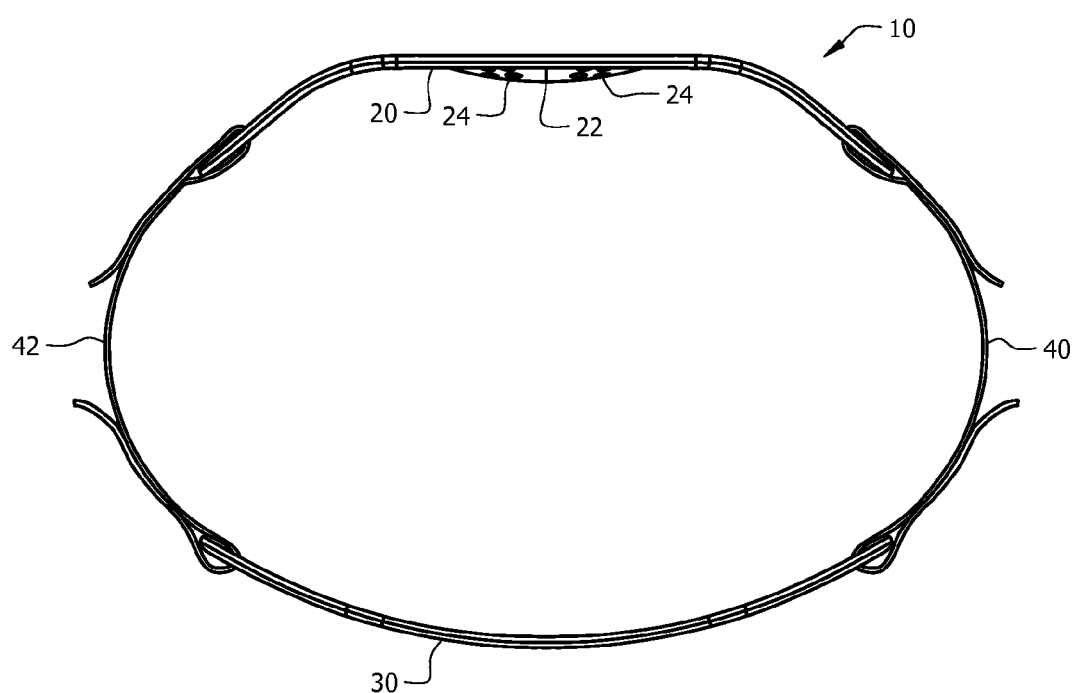
FIG. 7 illustrates a top plan view of the present invention.

When looking at the lumbar support member 20 from the top as shown in FIG. 7, the overall shape is somewhat circular or oval resembling the overall cross-sectional shape of the human body at the abdomen. However, the central portion of the lumbar support member 20 includes a centrally positioned convex dome 22 that protrudes into the back lumbar area of the lower lumbar region of the user. When worn, the convex dome 22 applies pressure on the lower lumbar area of the back.

FIG. 8 shows an exploded view of the back belt 10 showing the relationship of the abdominal support member 30, the lumbar support member 20, the left fastening belt 40 and the right fastening belt 42. In this view, it is shown that the surface of the fastening belts 40/42 facing away from the wearer have hook 44 and loop material 46 covering enough of the outwardly facing surface of the fastening belts 40/42 as to provide a strong, yet removable connection when the ends of the fastening belts 40/42 with the hook material 44 are looped back on the outward facing surface of the fastening belts 40/42 having the loop material 46. In the preferred embodiment, loop material 46 is present in the majority length of the outside surface of the fastening belts 40/42 to provide a wide range of adjustability. It should be noted that in some embodiments, the hook material 44 is swapped with the loop material 46. Additionally, it is anticipated that the hook material 44 and the loop material 46 may cover less than 100% of the width of the outer surfaces of the fastening belts 40/42 as required for proper adhesion.

Figure 9:
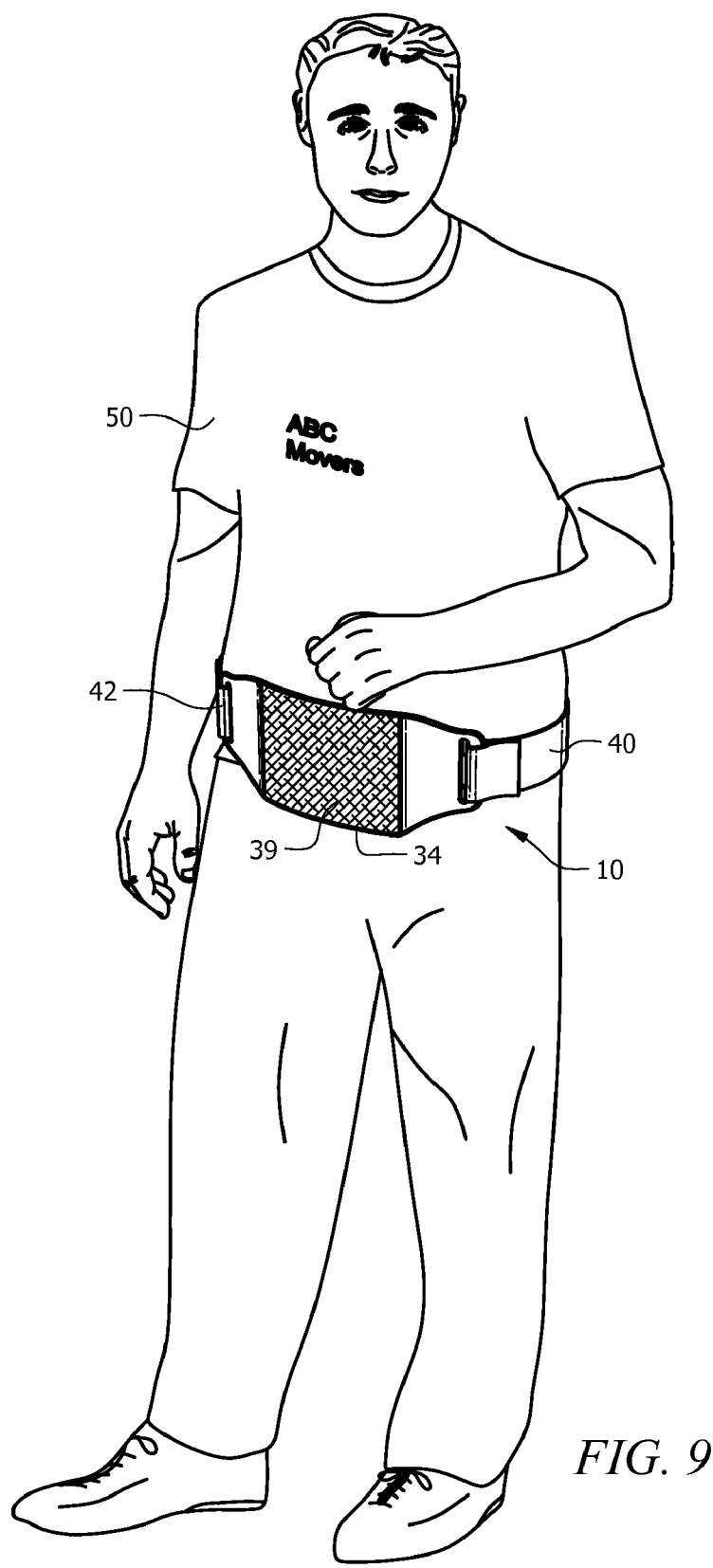
FIG. 9 illustrates a perspective view of the present invention in use.

FIG. 9 shows the back belt 10 being worn by a user 50. The abdominal support member 30 is shown with the sleeve 39. Also visible are the fastening belts 40/42. The lumbar support member 20 is not visible in this view.

In addition to the structural portions of the support members as described herein, in some embodiments, the back belt includes a pouch for storage of personal items and/or a holder for a personal audio device, a personal communication device, cell phone or the like. In yet another embodiment, the rear support member includes a pouch (not shown) for storing a hot or cold pack for hot or cold therapy.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. In a brace for supporting a user's abdomen and lumbar region, the brace having an abdominal support member, a lumbar support member connected by a pair of belts and a convex dome located on the lumbar support member, the improvement comprising:

a first belt of the pair of belts passing through a left slot of the abdominal support member and through a left slot of the lumbar support member and a second belt of the pair of belts passing through a right slot of the abdominal support member and through a right slot of the lumbar support member, the right slot of the abdominal support member and the left slot of the abdominal support member being substantially vertical and equally sized, and the right slot of the lumbar support member and the left slot of the lumbar support member being substantially vertical and equally sized;

the right slot of the abdominal support member having a top and a bottom, and the left slot of the abdominal support member having a top and a bottom, the top of the right slot of the abdominal support member having the same vertical position as the top of the left slot of the abdominal support member, and the bottom of the right slot of the abdominal support member having the same vertical position as the bottom of the left slot of the abdominal support member, where vertical is the orientation of the right slot of the abdominal support member and left slot of the abdominal support member when the brace is in use;

the right slot of the lumbar support member having a top and a bottom, and the left slot of the lumbar support member having a top and a bottom, the top of the right slot of the lumbar support member having the same vertical position as the top of the left slot of the lumbar support member, and the bottom of the right slot of the lumbar support member having the same vertical position as the bottom of the left slot of the lumbar support member, where vertical is the orientation of the right slot of the lumbar support member and the left slot of the lumbar support member when the brace is in use;

the convex dome of the lumbar support member bulging inward toward the user, with the convex dome designed to support the lumbar region of the user;

an outside surface of the first and second belts substantially covered by hook and loop material, the first belt passing through the left slot of the abdominal support member and the left slot of the lumbar support member, the second belt passing through the right slot of the abdominal support member and the right slot of the lumbar support member, the hook and loop material allowing the first and second belts to be doubled over onto themselves to tighten the back brace around a waist of a user;

a top central edge of the abdominal support member and a bottom central edge of the abdominal support member being substantially straight;

a first vertical distance between the top of the left slot of the abdominal support member and the top central edge of the abdominal support member, and a second vertical distance between the top central edge of the abdominal support member and the top of the right slot of the abdominal support member;

a third vertical distance between the bottom of the left slot of the abdominal support member and the bottom central edge of the abdominal support member, and a fourth vertical distance between the bottom of the right slot of the abdominal support member and the bottom central edge of the abdominal support member;

the first vertical distance being equal to the second vertical distance, the third vertical distance being equal to the fourth vertical distance, the first and second vertical distances being less than the third and fourth vertical distances such that protrusion into a ribcage of the user is minimized;

and a top central edge of the lumbar support member and a bottom central edge of the lumbar support member being substantially straight;

a fifth vertical distance between the top of the left slot of the lumbar support member and the top central edge of the lumbar support member, and a sixth vertical distance between the top central edge of the lumbar support member and the top of the right slot of the lumbar support member;

a seventh vertical distance between the bottom of the left slot of the lumbar support member and the bottom central edge of the lumbar support member, and a eighth vertical distance between the bottom of the right slot of the lumbar support member and the bottom central edge of the lumbar support member;

the fifth vertical distance being equal to the sixth vertical distance, the seventh vertical distance being equal to the eighth vertical distance;

the fifth and sixth vertical distances being less than the seventh and eight vertical distances;

the third and fourth vertical distances being less than the seventh and eighth vertical distances;

a first sleeve covering a front and back surface of the abdominal support member between the top central edge of the abdominal support member and bottom central edge of the abdominal support member; and a second sleeve covering a front and back surface of the lumbar support member between the top central edge of the lumbar support member and bottom central edge of the lumbar support member.

2. The brace according to claim 1, further comprising a plurality of circular air vents in the lumbar support member.

3. The brace according to claim 1, further comprising a plurality of circular air vents in the abdominal support member.

4. The brace according to claim 1, wherein an outside end portion of each belt comprises hook material and a remainder of the outer length of each belt comprises loop material.

5. The brace according to claim 1, wherein an outside end portion of each belt comprises loop material and a remainder of the outer length of each belt comprises loop material.

6. In a brace for supporting a user's abdomen and lumbar region, the brace having an abdominal support member, a lumbar support member connected by a pair of belts and a convex dome located on the lumbar support member, the improvement consisting of:

a left slot at a first end of the abdominal support member and a right slot at a second end of the abdominal support member;

a left slot at a first end of the lumbar support member and a right slot at a second end of the lumbar support member;

a first belt of the pair of belts passing through the left slot of the abdominal support member and through the left slot of the lumbar support member and a second belt of the pair of belts passing through the right slot of the abdominal support member and through the right slot of the lumbar support member;

the right slot of the abdominal support member and the left slot of the abdominal support member being substantially vertical and equally sized, where vertical is the orientation of the right slot of the abdominal support member and left slot of the abdominal support member when the brace is in use, and the right slot of the lumbar support member and the left slot of the lumbar support member being substantially vertical and equally sized, where vertical is the orientation of the right slot of the lumbar support member and left slot of the lumbar support member when the brace is in use;

wherein the right slot of the abdominal support member and the left slot of the abdominal support member, and the right slot of the lumbar support member and left slot of the lumbar support member, are all of equal size;

the right slot of the abdominal support member having a top and a bottom, and the left slot of the abdominal support member having a top and a bottom;

the right slot of the lumbar support member having a top and a bottom, and the left slot of the lumbar support member having a top and a bottom;

an outside surface of the first and second belts substantially covered by hook and loop material so that the first and second belts passing through the left slot of the abdominal support member and the right slot of the abdominal support member, and the left slot the lumbar support member and the right slot of the abdominal support member, can be doubled over onto themselves to tighten the brace around a waist of a user;

a top central edge of the abdominal support member and a bottom central edge of the abdominal support member having a straight configuration and being substantially horizontal with respect to the top of the left slot of the abdominal support member and the top of the right slot of the abdominal support member, a first vertical distance between the top of the left slot of the abdominal support member and the top central edge of the abdominal support member, and a second vertical distance between the top central edge of the abdominal support member and the top of the right slot of the abdominal support member;

a third vertical distance between the bottom of the left slot of the abdominal support member and the bottom central edge of the abdominal support member, and a fourth vertical distance between the bottom of the right slot of the abdominal support member and the bottom central edge of the abdominal support member;

the first vertical distance being equal to the second vertical distance, the third vertical distance being equal to the fourth vertical distance, the first and second vertical distances being less than the third and fourth vertical distances such that protrusion into a ribcage of the user is minimized, creating a downward bias of material such that more material is present below the bottom of the left slot of the abdominal support member and the bottom of the right slot of the abdominal support member than above the top of the left slot of the abdominal support member and the top of the right slot of the abdominal support member;

and a top central edge of the lumbar support member and a bottom central edge of the lumbar support member having a straight configuration;

a fifth vertical distance between the top of the left slot of the lumbar support member and the top central edge of the lumbar support member, and a sixth vertical distance between the top central edge of the lumbar support member and the top of the right slot of the lumbar support member;

a seventh vertical distance between the bottom of the left slot of the lumbar support member and the bottom central edge of the lumbar support member, and a eighth vertical distance between the bottom of the right slot of the lumbar support member and the bottom central edge of the lumbar support member;

the fifth vertical distance being equal to the sixth vertical distance, the seventh vertical distance being equal to the eighth vertical distance;

the fifth and sixth vertical distances being less than the seventh and eight vertical distances;

the third and fourth vertical distances being less than the seventh and eighth vertical distances;

a first sleeve covering a front and back surface of the abdominal support member between the top central edge abdominal support member and bottom central edge of the abdominal support member; and a second sleeve covering a front and back surface of the lumbar support member between the top central edge and bottom central edge of the lumbar support member;

wherein the user wears the brace with the abdominal support member against the user's abdomen, and the lumbar support member against the lumbar region, allowing the convex dome of the lumbar support member to support the user's lumbar region.

7. The brace according to claim 6, further comprising a plurality of circular air vents in the lumbar support member.

8. The brace according to claim 6, further comprising a plurality of circular air vents in the abdominal support member.

9. The brace according to claim 6, wherein an outside end portion of each belt comprises hook material and a remainder of the outer length of each belt comprises loop material.

10. The brace according to claim 6, wherein an outside end portion of each belt comprises loop material and a remainder of the outer length of each belt comprises loop material.

11. In a brace for supporting a user's abdomen and lumbar region, the brace having an abdominal support member, a lumbar support member connected by a pair of belts and a convex dome located on the lumbar support member, the improvement comprising:

a plurality of circular air vents in the lumbar support member;

a plurality of circular air vents in the abdominal support member;

a first belt of the pair of belts passing through a left slot of the abdominal support member and through a left slot of the lumbar support member and a second belt of the pair of belts passing through a right slot of the abdominal support member and through a right slot of the lumbar support member, the right slot of the abdominal support member and the left slot of the abdominal support member being substantially vertical and equally sized, where vertical is the orientation of the right slot of the abdominal support member and left slot of the abdominal support member when the brace is in use, and the right slot of the lumbar support member and the left slot of the lumbar support member being substantially vertical and equally sized, where vertical is the orientation of the right slot of the abdominal support member and left slot of the abdominal support member when the brace is in use;

the right slot of the abdominal support member having a top and a bottom, and the left slot of the abdominal support member having a top and a bottom;

the left slot of the lumbar support member having a top and a bottom, and the right slot of the lumbar support member having a top and a bottom;

the abdominal support member of a smaller size than the lumbar support member, the abdominal support member shaped to support the user's abdomen, the lumbar support member shaped to conform to the user's lumbar region;

the abdominal support member positioned against the user's abdomen, the lumbar support member positioned against the user's lumbar region;

an outside surface of the first and second belts substantially covered by hook and loop material so that the first and second belts passing through the left slot of the abdominal support member and the right slot of the abdominal support member, and the left slot of the lumbar support member and right slot of the lumbar support member can be doubled over onto themselves to tighten the back brace around a waist of a user;

a top central edge/a bottom central edge of the abdominal support member having a straight configuration and being substantially horizontal with respect to the top of the left slot/top of the right slot of the abdominal support member, a first vertical distance between the top of the left slot of the abdominal support member and the top central edge of the abdominal support member, and a second vertical distance between the top central edge of the abdominal support member and the top of the right slot of the abdominal support member;

a third vertical distance between the bottom of the left slot of the abdominal support member and the bottom central edge of the abdominal support member, and a fourth vertical distance between the bottom of the right slot of the abdominal support member and the bottom central edge of the abdominal support member;

the first vertical distance being equal to the second vertical distance, the third vertical distance being equal to the fourth vertical distance, the first and second vertical distances being less than the third and fourth vertical distances such that protrusion into a ribcage of the user is minimized;

and a top central edge/a bottom central edge of the lumbar support member having a straight configuration;

a fifth vertical distance between the top of the left slot of the lumbar support member and the top central edge of the lumbar support member, and a sixth vertical distance between the top central edge of the lumbar support member and the top of the right slot of the lumbar support member;

a seventh vertical distance between the bottom of the left slot of the lumbar support member and the bottom central edge of the lumbar support member, and a eighth vertical distance between the bottom of the right slot of the lumbar support member and the bottom central edge of the lumbar support member;

the fifth vertical distance being equal to the sixth vertical distance the seventh vertical distance being equal to the eighth vertical distance;

the fifth and sixth vertical distances being less than the seventh and eighth vertical distances;

the third and fourth vertical distances being less than the seventh and eighth vertical distances;

a first sleeve covering a front and back surface of the abdominal support member between the top central edge and bottom central edge of the abdominal support member; and a second sleeve covering a front and back surface of the lumbar support member between the top central edge and bottom central edge of the lumbar support member.

12. The brace according to claim 11, wherein an outside end portion of each belt comprises hook material and a remainder of the outer length of each belt comprises loop material.

13. The brace according to claim 11, wherein an outside end portion of each belt comprises loop material and a remainder of the outer length of each belt comprises loop material.

* * * * *